(12) United States Patent
Litvak et al.

(10) Patent No.: US 9,050,467 B2
(45) Date of Patent: *Jun. 9, 2015

(54) COMPENSATION CURRENT OPTIMIZATION FOR COCHLEAR IMPLANT SYSTEMS

(71) Applicant: Advanced Bionics AG, Staefa (CH)

(72) Inventors: Leonid M. Litvak, Los Angeles, CA (US); Aniket Saoji, Ann Arbor, MI (US)

(73) Assignee: Advanced Bionics AG, Staefa (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/272,349

(22) Filed: May 7, 2014

(65) Prior Publication Data
US 2014/0243928 A1    Aug. 28, 2014

Related U.S. Application Data

(63) Continuation of application No. 13/956,292, filed on Jul. 31, 2013, now Pat. No. 8,761,894, which is a continuation of application No. 13/425,770, filed on Mar. 21, 2012, now Pat. No. 8,509,907, which is a continuation of application No. 12/644,350, filed on Dec. 22, 2009, now Pat. No. 8,165,690.

(60) Provisional application No. 61/140,458, filed on Dec. 23, 2008, provisional application No. 61/224,844, filed on Jul. 10, 2009.

(51) Int. Cl.
*A61N 1/00* (2006.01)
*A61N 1/36* (2006.01)
*A61N 1/05* (2006.01)

(52) U.S. Cl.
CPC ........... *A61N 1/36032* (2013.01); *A61N 1/0541* (2013.01)

(58) Field of Classification Search
CPC .................. A61N 1/36032; A61N 1/0541
USPC ........................................... 607/57
See application file for complete search history.

(56) References Cited

U.S. PATENT DOCUMENTS 4,526,081 A    7/1985    Deutsch
(Continued)

OTHER PUBLICATIONS

Wilson, Blake S., et al., "Speech Processors for Auditory Prostheses", Third Quarterly Progress Report, (Feb.-Apr. 1993).
ISR & Written Opinion received in PCT Patent Application No. PCT/US09/69168 dated Mar. 11, 2010.
(Continued)

*Primary Examiner* — George Manuel
(74) *Attorney, Agent, or Firm* — ALG Intellectual Property, LLC

(57) ABSTRACT

An exemplary system includes a sound processor configured to process one or more audio signals and an implantable cochlear stimulator configured to apply stimulation representative of the one or more audio signals to a patient via a plurality of electrodes. In some embodiments, the sound processor directs the implantable cochlear stimulator to 1) apply a main current to a first electrode included in the plurality of electrodes and associated with a first pitch, 2) concurrently apply, during the application of the main current, a compensation current to a second electrode included in the plurality of electrodes and associated with a second pitch that is lower than the first pitch, and 3) adjust the compensation current to result in a target pitch being presented to the patient, the target pitch being higher than the first pitch.

20 Claims, 12 Drawing Sheets

(56) References Cited

U.S. PATENT DOCUMENTS

| | | |
|---|---|---|
| 6,970,570 B2 | 11/2005 | Goldstein |
| 7,130,694 B1 | 10/2006 | Voelkel |
| 7,206,640 B1 | 4/2007 | Overstreet |
| 7,251,530 B1 | 7/2007 | Overstreet et al. |
| 7,835,799 B1 * | 11/2010 | Segel et al. ............ 607/57 |
| 7,885,714 B2 | 2/2011 | Loeb |
| 2006/0100672 A1 | 5/2006 | Litvak |
| 2007/0179565 A1 | 8/2007 | Overstreet et al. |

OTHER PUBLICATIONS

Non-Final Office Action received in U.S. Appl. No. 12/644,350.
Non-Final Office Action received in U.S. Appl. No. 13/425,770, dated Jan. 22, 2013.
Extended European Search Report received in European Patent Application No. 09835749.4, dated Nov. 9, 2012.
Communication pursuant to Article 94(3) EPC received in European Patent Application No. 09835749.4, dated Jul. 2, 2013.
Non-Final Office Action received in U.S. Appl. No. 13/956,292, dated Oct. 28, 2013.

* cited by examiner

COMPENSATION CURRENT OPTIMIZATION FOR COCHLEAR IMPLANT SYSTEMS

RELATED APPLICATIONS

The present application is a continuation application of U.S. patent application Ser. No. 13/956,292, filed Jul. 31, 2013, which application is a continuation of U.S. patent application Ser. No. 13/425,770, filed Mar. 21, 2012, now issued as U.S. Pat. No. 8,509,907, which application is a continuation of U.S. patent application Ser. No. 12/644,350, filed Dec. 22, 2009, now issued as U.S. Pat. No. 8,165,690, which claims priority under 35 U.S.C. §119(e) to U.S. Provisional Patent Application No. 61/140,458, filed on Dec. 23, 2008, and to U.S. Provisional Patent Application No. 61/224,844, filed on Jul. 10, 2009. All of these applications are incorporated herein by reference in their respective entireties.

BACKGROUND

The sense of hearing in human beings involves the use of hair cells in the cochlea that convert or transduce audio signals into auditory nerve impulses. Hearing loss, which may be due to many different causes, is generally of two types: conductive and sensorineural. Conductive hearing loss occurs when the normal mechanical pathways for sound to reach the hair cells in the cochlea are impeded. These sound pathways may be impeded, for example, by damage to the auditory ossicles. Conductive hearing loss may often be helped by the use of conventional hearing aids that amplify sound so that audio signals reach the cochlea and the hair cells. Some types of conductive hearing loss may also be treated by surgical procedures.

Sensorineural hearing loss, on the other hand, is due to the absence or the destruction of the hair cells in the cochlea which are needed to transduce audio signals into auditory nerve impulses. Thus, many people who suffer from severe to profound sensorineural hearing loss are unable to derive any benefit from conventional hearing aid systems.

To overcome sensorineural hearing loss, numerous cochlear implant systems, or cochlear prosthesis, have been developed. Cochlear implant systems bypass the hair cells in the cochlea by presenting electrical stimulation directly to the auditory nerve fibers. Direct stimulation of the auditory nerve fibers leads to the perception of sound in the brain and at least partial restoration of hearing function. To facilitate direct stimulation of the auditory nerve fibers, an array of electrodes may be implanted in the cochlea. The electrodes form a number of stimulation channels through which electrical stimulation pulses may be applied directly to auditory nerves within the cochlea.

Hence, an audio signal may be presented to a patient by processing and translating the audio signal into a number of electrical stimulation pulses. The stimulation pulses may then be applied directly to auditory nerves within the cochlea via one or more of the stimulation channels. In conventional cochlear implants, the array of electrodes in the cochlea cannot present a full spectrum of audible sound to the patient. There are often sounds having pitches that are higher or lower than pitches that can be generated by stimulating the array of cochlear implant electrodes under typical stimulation conditions. Additionally, apical or basal electrodes sometimes lose functionality after being used for an extended period of time, effectively reducing the spectrum of frequencies that can be presented to the patient by the cochlear implant. In many cases, it is desirable to extend the range of frequencies that can be presented to the patient without introducing additional electrodes or replacing non-functional electrodes through invasive procedures.

SUMMARY

An exemplary cochlear stimulation method includes 1) applying a main current to a first electrode associated with a first pitch and disposed within a cochlea of a patient, 2) concurrently applying a compensation current to a second electrode disposed within the cochlea and associated with a second pitch during the application of the main current, the compensation current being out-of-phase with the main current, and 3) optimizing an amount of the compensation current to result in a target pitch being presented to the patient that is distanced from the first pitch in a pitch direction opposite a pitch direction of the second pitch in relation to the first pitch.

Another exemplary cochlear stimulation method includes 1) applying a main current to a first electrode associated with a first pitch and disposed within a cochlea of a patient, 2) concurrently applying, during the application of the main current, a compensation current to at least one other electrode disposed within the cochlea and associated with at least one other pitch that is lower than the first pitch, and 3) adjusting the compensation current to result in a target pitch being presented to the patient, the target pitch being higher than the first pitch.

Another exemplary cochlear stimulation method includes 1) applying a main current to a first electrode associated with a first pitch and disposed within a cochlea of a patient, 2) concurrently applying, during the application of the main current, a compensation current to at least one other electrode disposed within the cochlea and associated with at least one other pitch that is higher than the first pitch, and 3) adjusting the compensation current to result in a target pitch being presented to the patient, the target pitch being lower than the first pitch.

An exemplary cochlear implant system includes a sound processor configured to process one or more audio signals and an implantable cochlear stimulator communicatively coupled to the sound processor and configured to apply stimulation representative of the one or more audio signals to a patient via a plurality of electrodes. The sound processor is configured to direct the implantable stimulator to 1) apply a main current to a first electrode included within the plurality of electrodes and associated with a first pitch, 2) concurrently apply a compensation current to a second electrode included within the plurality of electrodes and associated with a second pitch during the application of the main current, the compensation current being out-of-phase with the main current, and 3) optimize an amount of the compensation current to result in a target pitch being presented to the patient that is distanced from the first pitch in a pitch direction opposite a pitch direction of the second pitch in relation to the first pitch.

BRIEF DESCRIPTION OF THE DRAWINGS

The accompanying drawings illustrate various embodiments of the principles described herein and are a part of the specification. The illustrated embodiments are merely examples and do not limit the scope of the disclosure.

Throughout the drawings, identical reference numbers designate similar, but not necessarily identical, elements.

DETAILED DESCRIPTION

Figure 1:
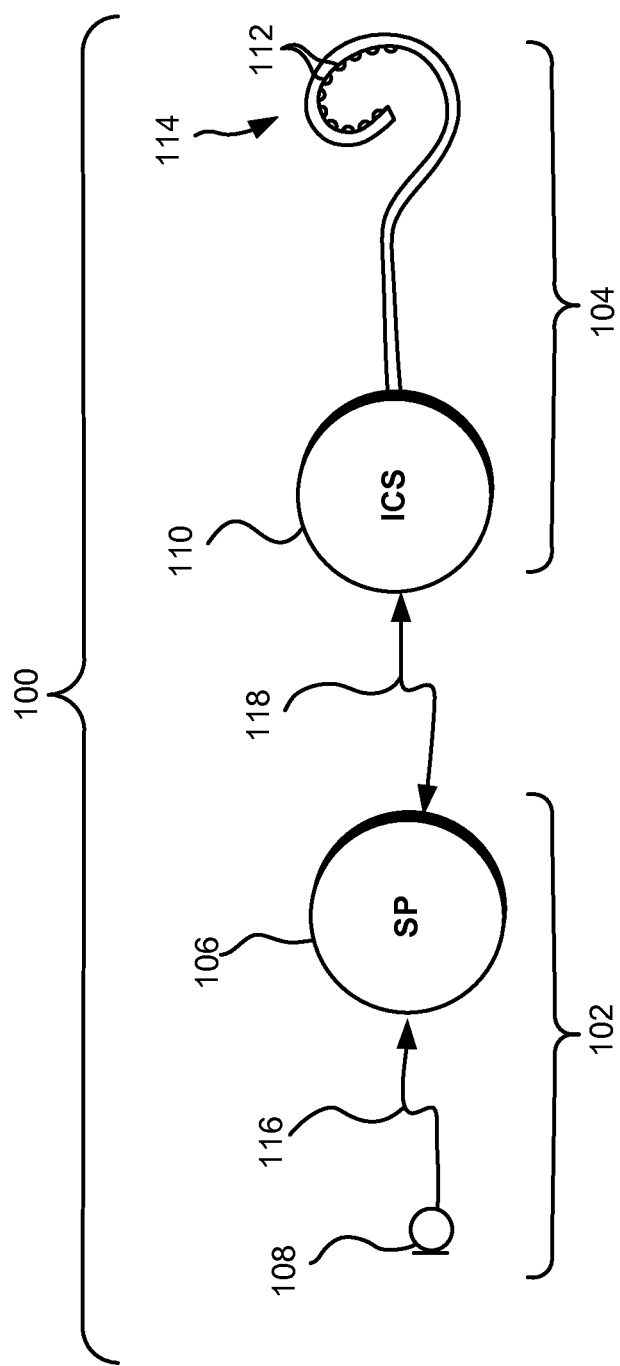
FIG. 1 illustrates an exemplary cochlear implant system according to principles described herein.

Methods and systems for applying stimulation current to a cochlear implant patient are described herein. In some examples, a sound processor is configured to process one or more audio signals. An implantable cochlear stimulator is communicatively coupled to the sound processor and configured to apply stimulation representative of the one or more audio signals to a patient via a plurality of electrodes. The sound processor may be configured to direct the implantable stimulator to concurrently apply a main current to a first electrode included within the plurality of electrodes and a compensation current to a second electrode included within the plurality of electrodes and associated with a second pitch. In some examples, the compensation current is out-of-phase with the main current. The sound processor may be further configured to direct the implantable cochlear stimulator to optimize an amount of the compensation current to result in a target pitch being presented to the patient that is distanced from the first pitch in a pitch direction opposite a pitch direction of the second pitch in relation to the first pitch. For example, the compensation current may be optimized to present a target pitch that is higher than the first pitch to the patient. Alternatively, the compensation current may be optimized to present a target pitch that is lower than the first pitch to the patient.

As will be described in more detail below, the methods and systems described herein allow a cochlear implant system to expand a range of pitches or frequencies that may be presented to a cochlear implant patient without introducing additional electrodes or replacing non-functional electrodes. Application of compensation current to one or more compensating electrodes in order to produce sound having a pitch that is lower than a pitch associated with a particular electrode (e.g., the most apical electrode) or a sound having a pitch that is higher than a pitch associated with a particular electrode (e.g., the most basal electrode) is referred to as "phantom electrode stimulation" in some of the examples given herein.

As used herein, an "incoming audio signal" may include speech, music, or other sounds as may serve a particular application and may include one or more perceptible attributes such as, but not limited to, words, lyrics, notes, musical patterns, harmonic relationships, pitches, and/or noises. In some examples, an incoming audio signal may also include noise.

In the following description, for purposes of explanation, numerous specific details are set forth in order to provide a thorough understanding of the present systems and methods. It will be apparent, however, to one skilled in the art that the present systems and methods may be practiced without these specific details. Reference in the specification to "one example" or "an example" means that a particular feature, structure, or characteristic described in connection with the example is included in at least one example. The appearance of the phrase "in one example" in various places in the specification are not necessarily all referring to the same example.

FIG. 1 illustrates an exemplary cochlear implant system 100 that may be used in accordance with the present methods and systems. Cochlear implant system 100 includes a sound processor portion 102 and a cochlear stimulation portion 104. The sound processor portion 102 may include a sound processor 106, a microphone 108, and/or additional circuitry as best serves a particular application. The cochlear stimulation portion 104 may include an implantable cochlear stimulator 110, a number of electrodes 112 disposed on a lead 114, and/or additional circuitry as best serves a particular application. The components within the sound processor portion 102 and the cochlear stimulation portion 104 will be described in more detail below.

The microphone 108 of FIG. 1 is configured to sense or detect audio signals and convert the sensed signals to corresponding electrical signals. In some examples, the audio signal may include speech. The audio signal may additionally or alternatively include music, noise, and/or other sounds. The electrical signals are sent from the microphone 108 to the sound processor 106 via a communication link 116. Alternatively, the microphone 108 may be connected directly to, or integrated with, the sound processor 106. The sound processor 106 is configured to process the converted audio signals in accordance with a selected sound processing strategy to generate appropriate stimulation parameters for controlling the implantable cochlear stimulator 110. These stimulation parameters may specify or define the polarity, magnitude, location (i.e., which electrode pair or electrode group receive the electrical stimulation), stimulation rate, timing (i.e., when the electrical stimulation is to be applied to a particular electrode pair), spectral tilt, and/or any other characteristic of the electrical stimulation that is generated by the implantable cochlear stimulator 110.

The lead 114 shown in FIG. 1 is configured to be inserted within a duct of a cochlea. As shown in FIG. 1, the lead 114 includes an array of electrodes 112, e.g., sixteen electrodes, spaced along its length. It will be understood, however, that any number of electrodes 112 may be disposed on the lead 114. As will be described in more detail below, electronic circuitry within the implantable cochlear stimulator 110 is configured to generate and apply electrical stimulation to one or more stimulation sites within the cochlea via selected stimulation channels (i.e., pairs or groups of the individual electrodes 112) in accordance with a specified stimulation strategy defined by the sound processor 106.

The implantable cochlear stimulator 110 and the sound processor 106 may be communicatively coupled via a suitable data or communication link 118. It will be understood that the communication link 118 may include a bi-directional communication link and/or one or more dedicated uni-directional communication links.

In some examples, the sound processor 106 and the microphone 108 comprise an external portion of the cochlear implant system 100 and the implantable cochlear stimulator 110 and the electrode lead 114 comprise an implantable portion of the system 100 that is implanted within a patient's body. In alternative embodiments, one or more portions of the sound processor 106 are included within the implantable portion of the cochlear implant system 100.

The external and implantable portions of the cochlear implant system 100 may each include one or more coils configured to transmit and receive power and/or control signals via the communication link 118. For example, the external portion of the cochlear implant system 100 may include an external coil (not shown) and the implantable portion of the cochlear implant system 100 may include an implantable coil (not shown). The external coil and the implantable coil may be inductively coupled to each other, thereby allowing data to be transmitted therebetween. The data may include, for example, the magnitude and polarity of a sensed audio signal. The external coil may also transmit power from the external portion to the implantable portion of the cochlear implant system 100.

It will be noted that, in some embodiments, both the sound processor 106 and the implantable cochlear stimulator 110 may be implanted within the patient, either in the same housing or in separate housings. If the sound processor 106 and the implantable cochlear stimulator 110 are in the same housing, the communication link 118 may be realized with a direct wire connection within such housing. If the sound processor 106 and the implantable cochlear stimulator 110 are in separate housings, the communication link 118 may include one or more inductive links, for example.

Figure 2:
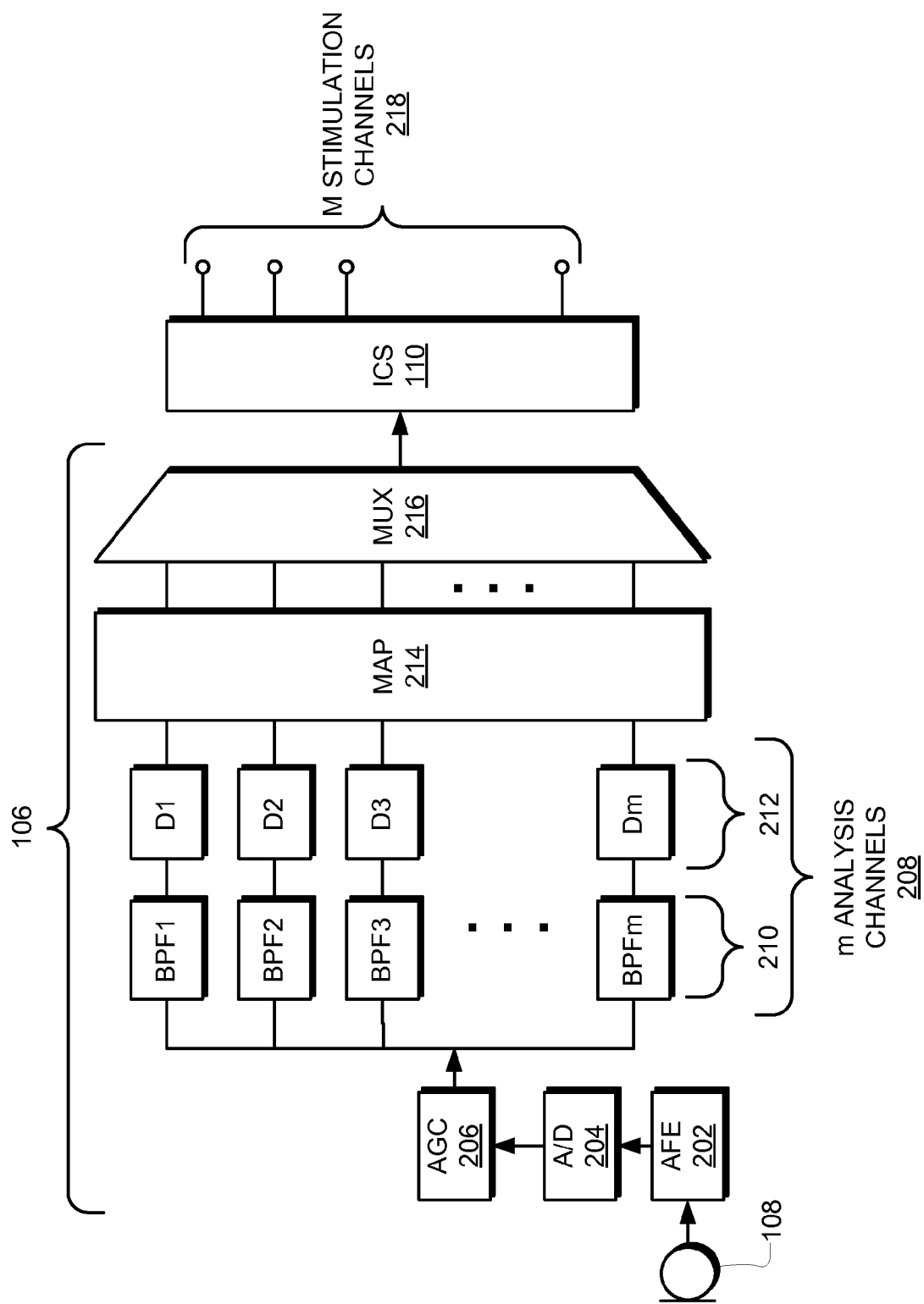
FIG. 2 is a functional block diagram of an exemplary sound processor and implantable cochlear stimulator according to principles described herein.

FIG. 2 is a functional block diagram of an exemplary sound processor 106 and implantable cochlear stimulator 110. The functions shown in FIG. 2 are merely representative of the many different functions that may be performed by the sound processor 106 and/or the implantable cochlear stimulator 110.

As shown in FIG. 2, the microphone 108 senses an audio signal, such as speech or music, and converts the audio signal into one or more electrical signals. These signals are then amplified in audio front-end (AFE) circuitry 202. The amplified audio signal is then converted to a digital signal by an analog-to-digital (A/D) converter 204. The resulting digital signal is then subjected to automatic gain control using a suitable automatic gain control (AGC) function 206.

After appropriate automatic gain control, the digital signal is processed in one of a number of digital signal processing or analysis channels 208. For example, the sound processor 106 may include, but is not limited to, eight analysis channels 208. Each analysis channel 208 may respond to a different frequency band of the sensed audio signal due to a series of band pass filters 210.

As shown in FIG. 2, each of the m analysis channels 208 may also include an energy detection stage (D1-Dm) 212. Each energy detection stage 212 may include any combination of circuitry configured to detect the amount of energy contained within each of the m analysis channels 208. For example, each energy detection stage 212 may include a rectification circuit followed by an integrator circuit.

After energy detection, the signals within each of the m analysis channels 208 are forwarded to a mapping stage 214. The mapping stage 214 is configured to map the signals in each of the m analysis channels 208 to one or more of M stimulation channels 218. In other words, the information contained in the m analysis channels 208 is used to define the electrical stimulation pulses that are applied to the patient by the implantable cochlear stimulator 110 via the M stimulation channels 218. As mentioned previously, pairs or groups of individual electrodes 112 may make up the M stimulation channels 218.

In some examples, the mapped signals are serialized by a multiplexer 216 and transmitted to the implantable cochlear stimulator 110. The implantable cochlear stimulator 110 may then apply electrical stimulation via one or more of the M stimulation channels 218 to one or more stimulation sites within the duct of the patient's cochlea. As used herein, the term "stimulation site" will be used to refer to a target area or location to which the electrical stimulation is applied. For example, a stimulation site may refer to any location within a region of auditory nerve tissue shown in FIG. 3.

Figure 3:
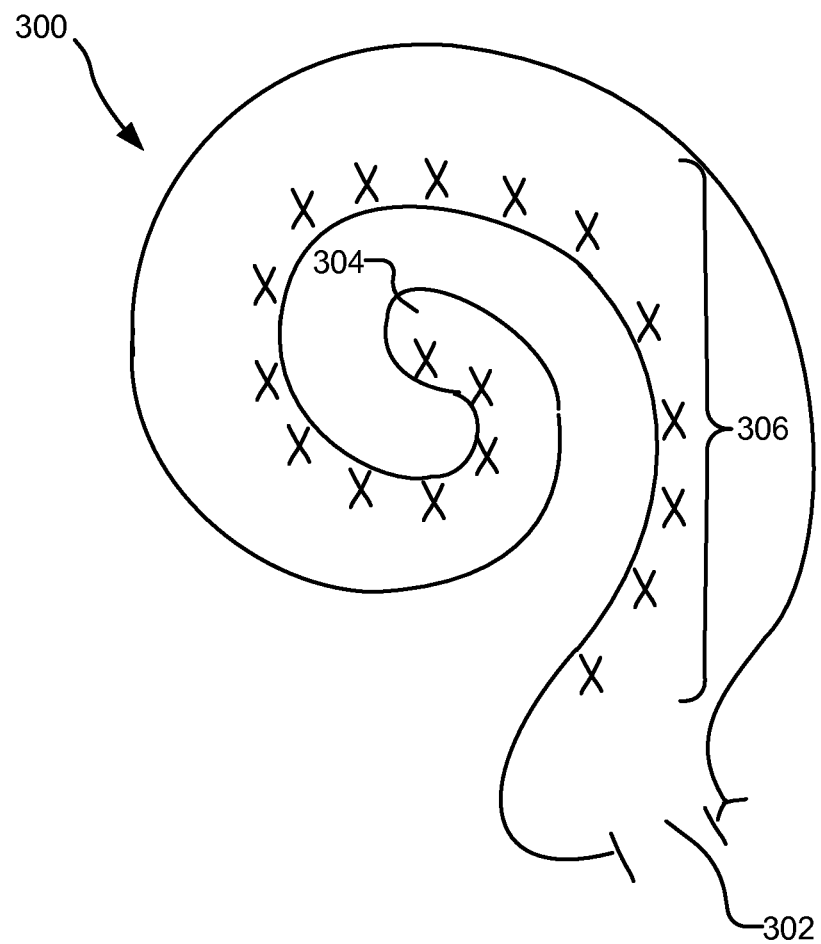
FIG. 3 illustrates a schematic structure of the human cochlea.

FIG. 3 illustrates a schematic structure of the human cochlea 300. As shown in FIG. 3, the cochlea 300 is in the shape of a spiral beginning at a base 302 and ending at an apex 304. Within the cochlea 300 resides auditory nerve tissue 306, which is denoted by Xs in FIG. 3. The auditory nerve tissue 306 is organized within the cochlea 300 in a tonotopic manner. Low frequencies are encoded at the apex 304 of the cochlea 300 while high frequencies are encoded at the base 302. Hence, each location along the length of the cochlea 300 corresponds to a different perceived frequency or pitch. A cochlear prosthesis, such as cochlear implant system 100, may therefore be implanted within a patient with sensorineural hearing loss and configured to apply electrical stimulation to different locations within the cochlea 300 to provide the sensation of hearing. The terms "perceived frequency" and "pitch" will be interchangeably used herein to refer to a frequency of a sound as perceived by a cochlear implant patient.

It is often desirable to convey sounds having pitches that are outside the range of pitches associated with the electrodes 112 of a cochlear implant system 100. For example, it may be desirable to convey a sound having a pitch that is lower than a pitch associated with the most apical electrode 112 or a sound having a pitch that is higher than a pitch associated with the most basal electrode 112. To this end, as will be described in more detail below, the systems and methods described herein are configured to concurrently apply stimulation current to two or more electrodes in order to produce a target pitch outside the range of pitches associated with the two or more electrodes 112.

Figure 4:
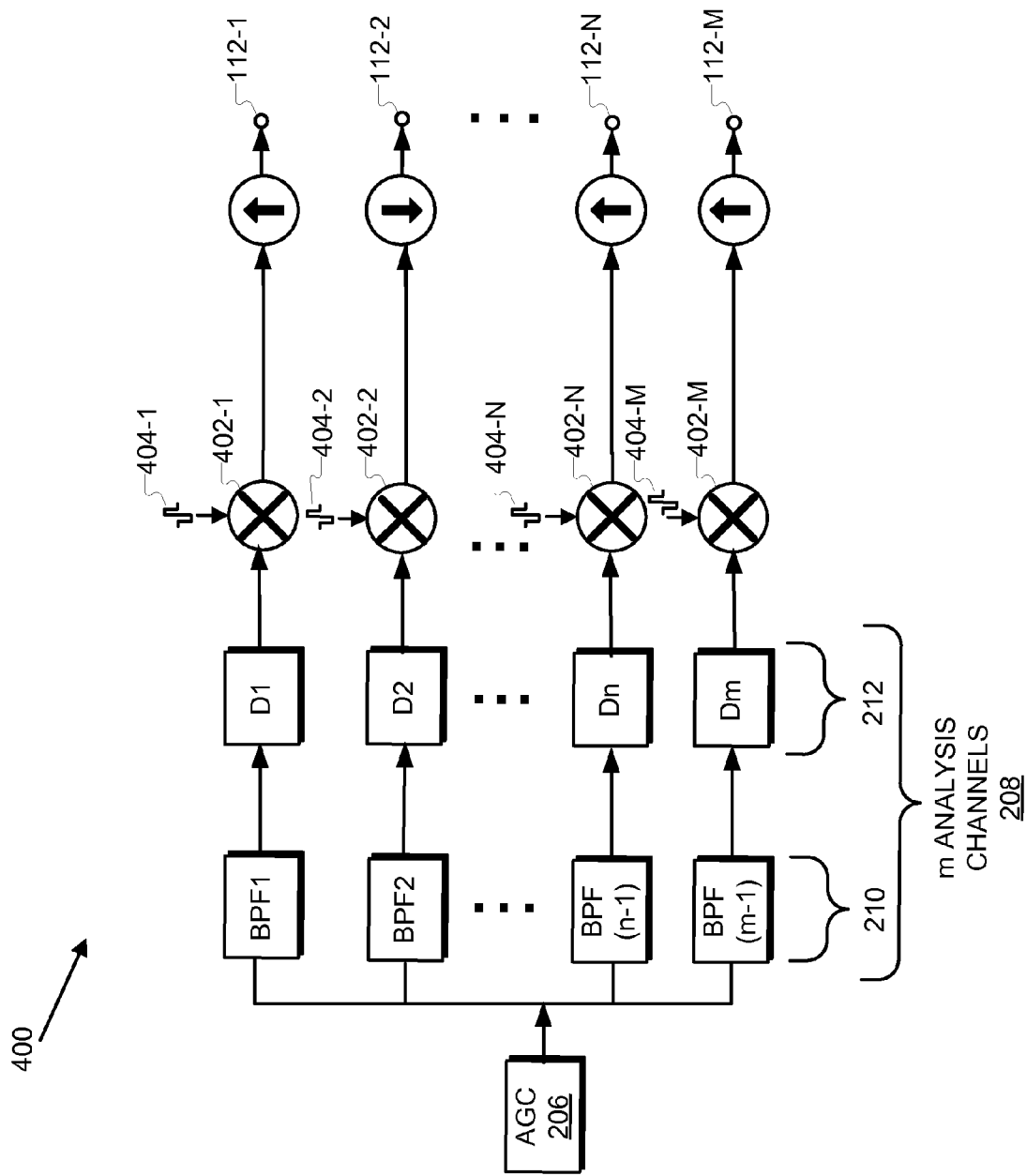
FIG. 4 is a functional block diagram of an exemplary stimulation strategy for applying current to two or more electrodes to produce a target pitch.

FIG. 4 is a functional block diagram of an exemplary stimulation strategy 400 for applying current to two or more electrodes 112 to produce a target pitch that is outside the range of pitches associated with electrodes 112. The components shown in FIG. 4 are exemplary only. Additional or alternative components may also be configured to perform the functions shown in FIG. 4. Moreover, the components may be included within the sound processor 106 and/or implantable cochlear stimulator 110 as may serve a particular application.

As depicted in FIG. 4, one or more multipliers (e.g., multipliers 402-1 though 402-M, collectively referred to herein as "multipliers 402") may be configured to multiply the signals generated by each of the analysis channels 208 with one or more carrier pulses (e.g., carrier pulses 404-1 through 404-M, collectively referred to herein as "carrier pulses 404") to generate pulses of electrical stimulation current that are delivered via one or more electrodes (e.g., electrodes 112-1 through 112-M, collectively referred to herein as "electrodes 112"). Each electrode 112 may be associated with a perceived frequency or pitch. In other words, stimulation current applied to a particular electrode 112 may cause a patient to hear or experience sound having a pitch associated with that electrode 112.

In some examples, electrode 112-1 may include the most apical electrode 112 that is functioning (i.e., not disabled) within a cochlear electrode array. Alternatively, electrode 112-1 may include the most basal functioning electrode 112 within a cochlear electrode array. It will be recognized that one or more of the electrodes 112 shown in FIG. 4 may correspond to one or more stimulation channels 218.

In some examples, the stimulation strategy 400 depicted in FIG. 4 is configured to use current steering to steer the current field generated by a main electrode (e.g., electrode 112-1) in order to generate a target pitch that is outside a range of pitches associated with electrodes 112. To facilitate current steering, the implantable cochlear stimulator 110 may include one or more components configured to select one or more electrodes 112 to serve as "compensating electrodes." Compensation current may be applied to the one or more compensating electrodes 112 at the same time a main current is applied to electrode 112-1. The compensation current is configured to steer a current field away from electrode 112-1 in a direction opposite that of the compensating electrodes 112. In this manner, a target pitch outside a range of pitches associated with electrodes 112 may be produced.

To illustrate, electrode 112-1 may include the most apical functioning electrode 112 within a cochlear electrode array. To produce a pitch lower than the pitch associated with electrode 112-1 (i.e., a pitch resulting from monopolar stimulation of electrode 112-1), compensation current may be applied to electrode 112-2. The compensation current steers a current field away from electrode 112-1 in a direction opposite that of electrode 112-2 to produce a pitch that is lower than the pitch associated with electrode 112-1.

In alternative examples wherein electrode 112-1 includes the most basal functioning electrode 112 within a cochlear electrode array, a pitch higher than the pitch associated with electrode 112-1 may be produced by applying compensation current to electrode 112-2. The compensation current steers a current field away from electrode 112-1 in a direction opposite that of electrode 112-2 to produce a pitch that is higher than the pitch associated with electrode 112-1.

In some examples, the current steering techniques described herein may be used to compensate for an electrode 112 that has become disabled or otherwise malfunctions. For example, the most basal and/or the most apical electrode 112 may become disabled. In order to obtain a pitch that is substantially similar to a pitch obtainable by the disabled electrode, a second most basal or second most apical electrode 112 may be stimulated with a main current at the same time compensation current is applied to one or more other electrodes 112.

In some examples, as shown in FIG. 4, the compensation current applied to a compensating electrode (e.g., electrode 112-2) is out-of-phase in relation to the main current applied to a main electrode (e.g., electrode 112-1). The compensation current may additionally or alternatively have a polarity opposite that of the main current.

In some examples, the amount of the main current applied to the main electrode 112-1 and the amount of the compensation current applied to the compensating electrode 112-2 may be optimized to produce a target pitch that is optimally distanced from the pitch associated with the main electrode 112-1. The optimally distanced target pitch may include a pitch that is maximally distanced from the pitch associated with the main electrode 112-1 in a direction opposite that of a pitch associated with the compensating electrode 112-2. For example, an optimal target pitch may include the lowest possible pitch that may be produced using current steering while staying within various operating parameters (e.g., most comfortable current levels, prosthesis compliance parameters, etc.). Additionally or alternatively, an optimal target pitch may include the highest possible pitch that may be produced using current steering while staying within the same operating parameters. An optimal target pitch may alternatively include any other target pitch outside the range of pitches associated with the electrodes 112.

A number of techniques for determining an optimal amount of compensation current that results in an optimal target pitch will now be described. It will be recognized that the techniques described herein are merely illustrative of the many different techniques that may be used in accordance with the systems and methods described herein.

In some examples, an optimal amount of compensation current may be determined by first determining a most comfortable current level corresponding to the main electrode 112-1 in a monopolar configuration (i.e., the compensating current is substantially equal to zero). As used herein, a "most comfortable current level" refers to a stimulation current level at which electrical stimulation is most comfortable to a patient. At the most comfortable current level, loud sounds should be sensed by the patient at a level that is perceived as loud, but not painfully loud. Likewise, soft sounds should be sensed by the patient at a level that is soft, but not so soft that the sounds are not perceived at all. The most comfortable current level typically varies depending on the patient and on the particular electrode 112 being stimulated.

The most comfortable current level corresponding to the main electrode 112-1 may be determined using any suitable method or technique, such as, for example, increasing or decreasing an amount of current applied to the electrode 112-1 until a patient indicates that the most comfortable current level has been reached. The amount of current corresponding to the most comfortable current level may be represented by "l(0)."

Once the most comfortable current level has been determined for the main electrode 112-1 in monopolar configuration, an initial ratio of compensation current to main current may be selected such that the compensation current is less than the main current. The ratio of the compensation current to the main current may be represented by "σ." Hence, the compensation current applied to compensating electrode 112-2 is equal to σ multiplied by the main current applied to main electrode 112-1. The sum of the main current and the compensation current may be referred to as the total current.

Any suitable σ may be selected as may serve a particular application. An exemplary, but not exclusive, value for σ is 0.8. The initial selection of σ may be based on any suitable factor or heuristic.

The main current is then applied to main electrode 112-1. Compensation current is concurrently applied to compensating electrode 112-2 in accordance with σ. The total current at the selected σ may be adjusted (e.g., increased) while the most comfortable current level is monitored. In some examples, the total current may be adjusted until a most comfortable current level corresponding to the concurrent application of current to electrodes 112-1 and 112-2 is obtained.

In some examples, as the total current applied to electrodes 112-1 and 112-2 is increased, a device compliance of the cochlear implant system 100 may be reached before the most comfortable current level for the total current is obtained. The device compliance refers to the maximum current that can be applied given the impedance of one or more of the electrodes 112 and the voltage constraints of the cochlear implant system 100. If the device compliance is reached, a may be reduced, and the most comfortable current level for the total current at the reduced a may then be determined.

The main current applied to electrode 112-1 may be represented by "l(σ)". Once the most comfortable current level for the total current has been determined at σ, a coefficient (K) may be determined according to Equation 1:

$$I(\sigma) = \frac{I(0)}{(1 - (K \cdot \sigma))} \quad \text{(Eq. 1)}$$

Once the coefficient K has been determined, Equation 1 may be used to change a while maintaining the total current at substantially the most comfortable current level. For example, for any selected σ, the amount of the main current l(σ) to be applied to electrode 112-1 may be determined in accordance with Equation 1. The amount of compensation current to be applied to electrode 112-2 may likewise be determined by multiplying l(σ) by σ.

Using Equation 1, appropriate current levels may be applied to electrodes 112-1 and 112-2 as σ is adjusted until an optimal target pitch is obtained. For example, the current applied to electrodes 112-1 and 112-2 may be adjusted in accordance with an adjustment of σ until a pitch that is substantially the furthest away from a pitch corresponding to main electrode 112-1 is obtained.

Once the optimal values for σ and the total current have been determined, a range of pitches between the optimal target pitch and the pitch corresponding to the main electrode 112-1 may be dynamically produced in substantially real-time signal processing. For example, Equation 1 may be used to determine appropriate main and compensation current levels as σ is changed to adjust the target pitch.

In some examples, the sound processor 106 may be configured to direct the implantable cochlear stimulator 110 to apply electrical stimulation to a cochlear implant patient in accordance with the desired pitches and current levels described above by adjusting one or more gain parameters corresponding to a main electrode (e.g., electrode 112-1) and one or more compensating electrodes (e.g., electrode 112-2). It will be recognized that gain adjustments may be made to any of the electrodes 112 as may serve a particular application.

To illustrate, an incoming audio signal may include a pitch within a particular analysis channel 208 that is outside the range of pitches attainable by monopolar stimulation of one more of the electrodes 112. Accordingly, the sound processor 106 may direct the implantable cochlear stimulator 110 to switch to a current steering mode wherein different amounts of electrical stimulation are applied concurrently to main electrode 112-1 and to compensating electrode 112-2 in order to produce the desired pitch. The amount of compensation current and main current applied to electrodes 112-2 and 112-1, respectively, as well as the ratio σ therebetween, may be determined using any of the techniques described herein.

Figure 5:
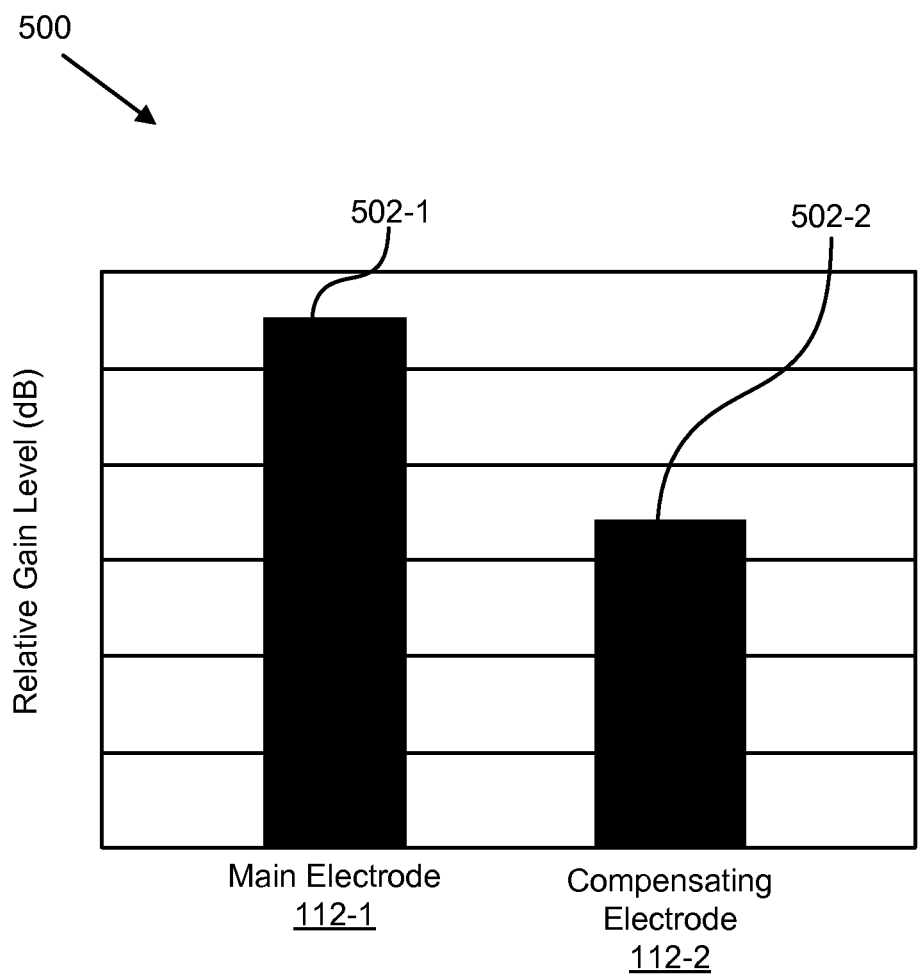
FIG. 5 depicts a graph showing exemplary gain parameter adjustments that may be performed according to principles described herein.

FIG. 5 depicts a graph 500 showing exemplary gain parameter adjustments that may be performed for a main electrode 112-2 and a compensating electrode 112-2. As depicted in FIG. 5, the sound processor 106 may adjust relative gain levels of gain parameters 502-1 and 502-2 corresponding to main electrode 112-1 and compensating electrode 112-2, respectively, such that a pitch perceived by a cochlear implant patient is substantially identical to the pitch in the incoming audio signal. Gain parameter 502-1 may adjust the amount of gain applied to the main current and the gain parameter 502-2 may adjust the amount of gain applied to the compensation current.

In some examples, the gain parameters 502-1 and 502-2 may be configured in accordance with a selected ratio (σ) of compensation current to main current corresponding to the particular pitch in the incoming audio signal. Additionally, the gain parameters 502-1 and 502-2 may be adjusted such that the total current applied to electrodes 112-1 and 112-2 is substantially at the most comfortable current level.

In some examples, a target pitch outside a range of pitches associated with electrodes 112 may be realized by applying compensation current to multiple electrodes 112. To illustrate, FIG. 6 is a functional block diagram of an exemplary stimulation strategy 600 wherein multiple electrodes 112 are designated as compensating electrodes in order to produce a desired target pitch.

Figure 6:
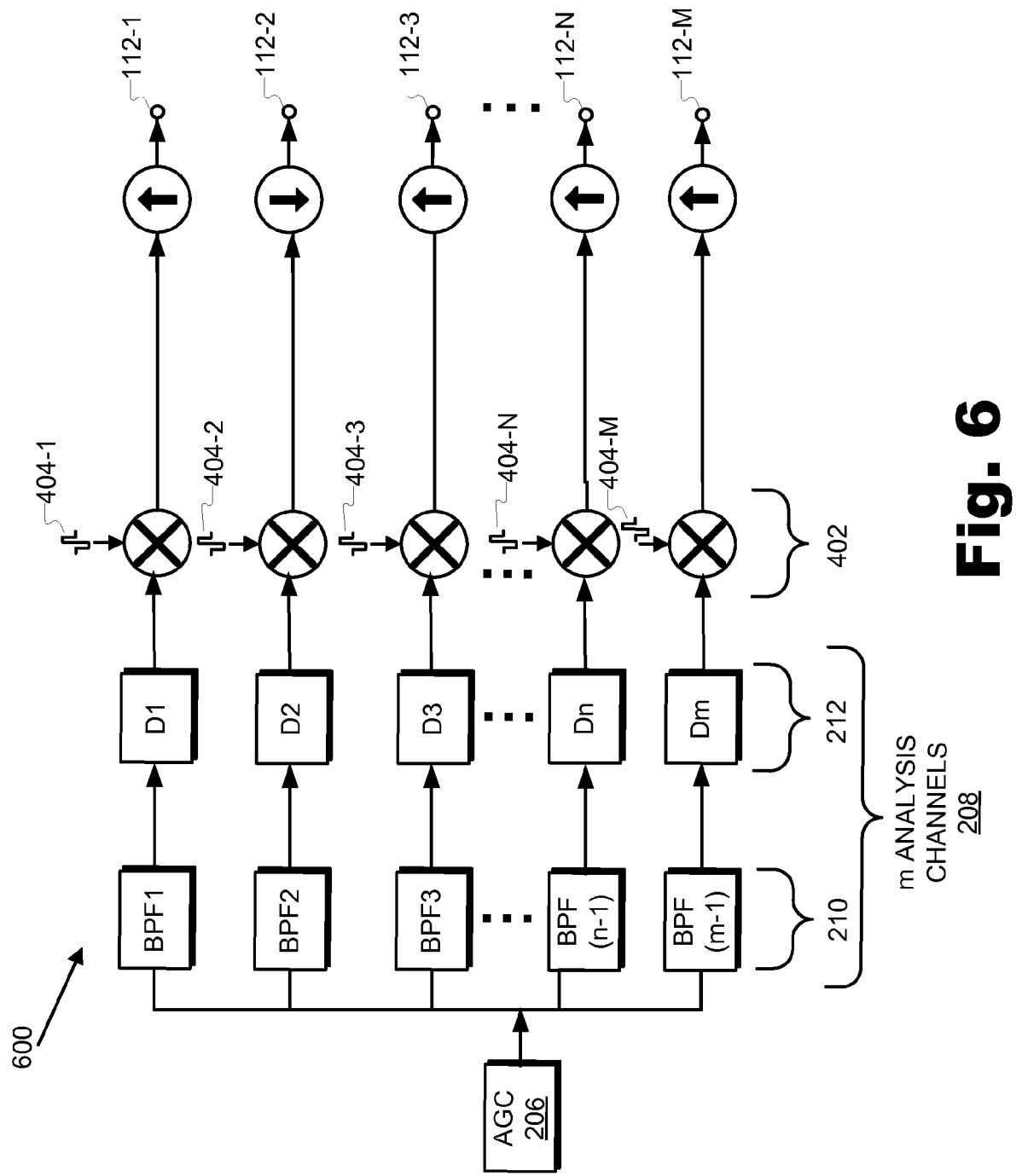
FIG. 6 is a functional block diagram of an exemplary stimulation strategy for applying current to a plurality of electrodes to produce a target pitch according to principles described herein.

As depicted in FIG. 6, a main electrode 112-1 may be adjacent to two compensating electrodes (e.g., electrodes 112-2 and 112-3). FIG. 6 shows two compensating electrodes for illustrative purposes only. It will be recognized that any number of compensating electrodes may be used as may serve a particular application. Pitches associated with the compensating electrodes 112-2 and 112-3 may be either higher or lower than the pitch associated with the main electrode 112-1 in monopolar configuration, depending on whether the main electrode 112-1 is an apical electrode or a basal electrode.

In some examples, the compensation current applied to at least one of the compensating electrodes 112-2 and 112-3 may have the same polarity as and/or may be in-phase with the main current applied to the main electrode 112-1. For example, a compensation current applied to the compensating electrode 112-2 may produce spurious stimulation or "side lobes" corresponding to a higher pitch than a pitch associated with the main electrode 112-1. The compensation current applied to the compensating electrode 112-2 may be out-of-phase with the main current applied to the main electrode 112-1. A compensation current that is in-phase with the main current and out-of-phase with the compensation current applied to the compensating electrode 112-2 may be applied to the compensating electrode 112-3 to at least partially cancel an undesired side lobe produced by the compensating electrode 112-2.

In some examples, the amount of main current applied to the main electrode 112-1 and the amount of compensation current applied to each of the compensating electrodes 112-2 and 112-3 may be optimized to produce a target pitch that is optimally distanced from the pitch associated with the main electrode 112-1 in a direction opposite that of the pitches associated with the compensating electrodes 112-2 and 112-3. These optimal current levels may be selected in accordance with any suitable method or technique. For example, the technique described above in connection with FIG. 4 may be adapted for multiple compensating electrodes 112.

To illustrate, a most comfortable current level corresponding to the main electrode 112-1 in a monopolar configuration may be determined as described above. The amount of current corresponding to the most comfortable current level may again be represented by "l(0)."

Once the most comfortable current level has been determined for the main electrode 112-1 in monopolar configuration, an initial ratio of compensation current applied to compensating electrode 112-2 to the main current is selected. This ratio may be represented by "a1". An initial ratio of compensation current applied to compensating electrode 112-3 to the main current is also selected. This ratio may be represented by "σ2". Any suitable values for σ1 and σ2 may be selected as serves a particular application. The sum of the main current, the compensation current applied to compensating electrode 112-1 (referred to herein as the "primary compensation current"), and the compensation current applied to compensating electrode 112-2 (referred to herein as the "secondary compensation current") may be referred to as the "total current".

The main current is then applied to main electrode 112-1. Compensation current is concurrently applied to compensating electrodes 112-2 and 112-3 in accordance with σ1 and σ2. The total current at the selected σ1 and σ2 may be adjusted (e.g., increased) while the most comfortable current level is monitored. In some examples, the total current may be adjusted until a most comfortable current level corresponding to the concurrent application of current to electrodes 112-1, 112-2, and 112-3 is obtained.

The main current applied to electrode 112-1 may be represented by "l(σ1,σ2)" when the total current is at the most comfortable current level and the ratios (σ1) and (σ2). Once the most comfortable current level for the total current has been determined at the ratios σ1 and σ2, coefficients K1 and K2 may be determined according to Equation 2:

$$I(\sigma 1, \sigma 2) = \frac{I(0)}{(1 - (K1 \cdot \sigma 1) \cdot (K2 \cdot \sigma 2))} \quad \text{(Eq. 2)}$$

Coefficients K1 and K2 in Equation 2 may be determined through any suitable technique, including interpolation. Once the coefficients K1 and K2 have been determined, Equation 2 may be used to change the ratios σ1 and σ2 while maintaining the total current at substantially the most comfortable current level. For example, for any selected ratios σ1 and σ2, the amount of the main current l(σ1, σ2) may be determined in accordance with Equation 2.

Using Equation 2, appropriate current levels may be applied to electrodes 112-1 through 112-3 as σ1 and σ2 are adjusted until an optimal target pitch is obtained.

Figure 7:
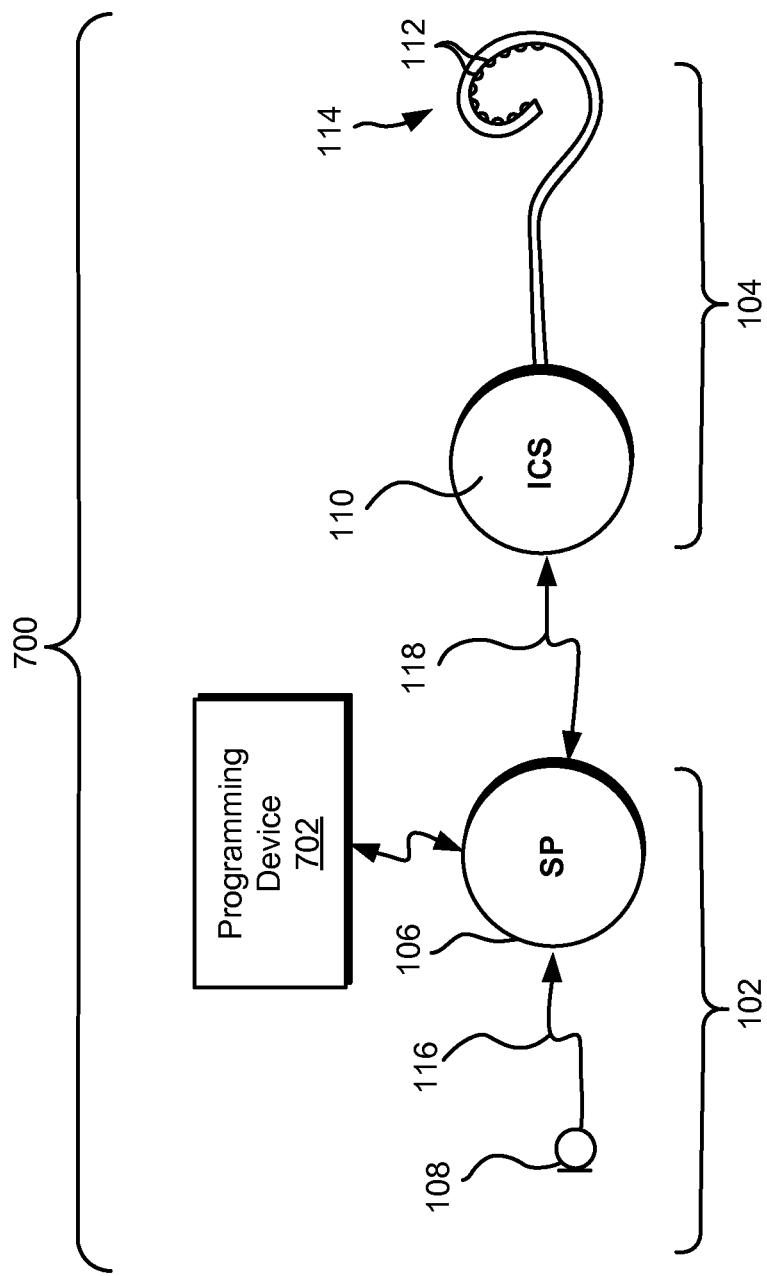
FIG. 7 illustrates an exemplary system configured to facilitate manual adjustment of one or more stimulation parameters to produce a target pitch.

In some examples, the patient and/or another user may manually adjust the ratio and/or amount of current applied to a main electrode (e.g., electrode 112-1) and one or more compensating electrodes (e.g., electrodes 112-2 and 112-3). FIG. 7 illustrates an exemplary cochlear implant system 700 configured to facilitate manual adjustment of stimulation channel parameters by a user.

As shown in FIG. 7, system 700 may include a programming device 702 selectively and communicatively coupled to the sound processor 106. The programming device 702 may include any combination of hardware, software, and firmware configured to perform any of the functions described herein. For example, the programming device 702 may include a fitting station, personal computer, handheld device (e.g., a personal digital assistant), a mobile device (e.g., a mobile telephone), and/or any other electronic device as may serve a particular application. As will be described in more detail below, the programming device 702 may be configured to direct the implantable cochlear stimulator 110 to apply electrical stimulation representative of an audio signal to a cochlear implant patient in accordance with one or more stimulation parameters.

Figure 8:
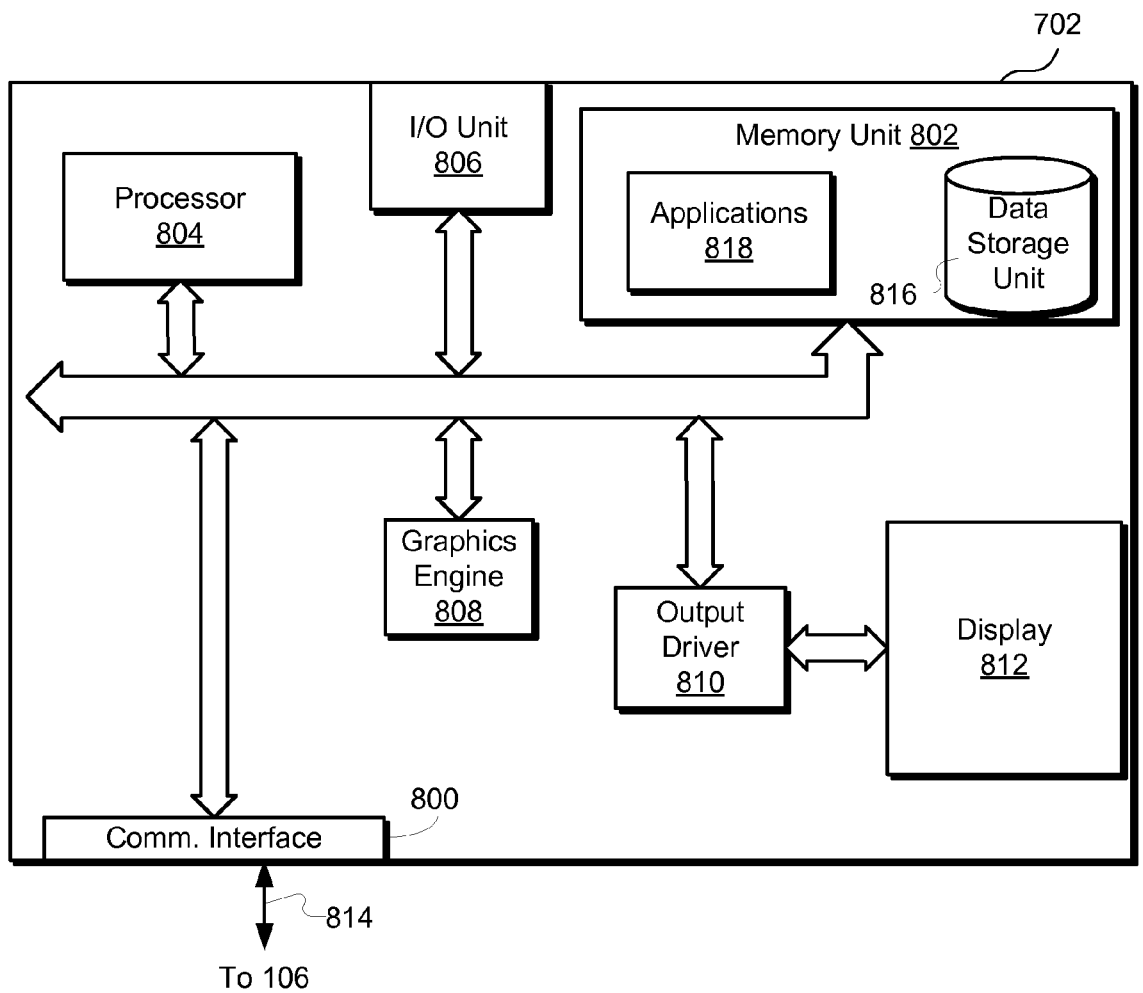
FIG. 8 illustrates a number of components that may be included within an exemplary programming device according to principles described herein.

FIG. 8 illustrates a number of components that may be included within an exemplary programming device 702. While an exemplary programming device 702 is shown in FIG. 8, the exemplary components illustrated in FIG. 8 are not intended to be limiting. Indeed, additional or alternative components and/or implementations may be included within the programming device 702.

In general, the programming device 702 may include any device configured to be selectively and communicatively coupled to one or more components of the cochlear implant system 100. For example, the programming device 702 may be selectively and communicatively coupled to the sound processor 106. Programming device 702 may also be configured to interact with various peripherals such as a terminal, keyboard, mouse, display screen, printer, stylus, input device(s), output device(s), and/or any other apparatus(es).

As shown in FIG. 8, the programming device 702 may include a communication interface 800, a programmable memory unit 802, a processor 804, an input/output unit 806 ("I/O unit 806"), a graphics engine 808, an output driver 810, and a display 812 communicatively connected to one another.

Communication interface 800 may be configured to transmit and receive data to and from the sound processor 106. Exemplary data transmitted from the programming device 702 to the sound processor 106 includes programming data such as stimulation parameters (e.g., gain parameters) and the like. Exemplary data received by the programming device 702 from the sound processor 106 includes status data representative of a status of one or more components of the sound processor 106 and/or the implantable cochlear stimulator 110.

In some examples, a communications link 814 may be used to facilitate communication between the programming device 702 and the sound processor 106. The communications link 814 may include any type of link used to transmit data, such as, but not limited to, an RF link, an infrared (IR) link, an optical link, a Bluetooth link, a thermal link, a wire link, or any other suitable link.

Programmable memory unit 802 may include, but is not limited to, FLASH memory, RAM, DRAM, or a combination thereof. The programmable memory unit 802 may additionally or alternatively include a data storage unit 816. The data storage unit 816 may include one or more data storage media, devices, or configurations and may employ any type, form, and combination of storage media. For example, the data storage unit 816 may include, but is not limited to, a hard drive, flash drive, optical disk, or other non-volatile storage unit. Data representative of one or more gain parameters and/or any other data may be stored within the data storage unit 816.

Processor 804 may be configured to control one or more operations of the components included within the programming device 702. Processor 804 may direct execution of operations in accordance with computer-executable instructions such as may be stored in memory unit 802.

I/O unit 806 may be configured to receive user input and provide user output and may include any hardware, firmware, software, or combination thereof supportive of input and output capabilities.

As instructed by processor 804, graphics engine 808 may generate graphics, which may include graphical user interfaces ("GUIs"). The output driver 810 may provide output signals representative of the graphics generated by graphics engine 808 to display 812. The display 812 may then present the graphics to the user.

One or more applications 818 may be executed by the programming device 702. The applications, or application clients, may reside in memory unit 802 or in any other area of the programming device 702 and be executed by the processor 804. Each application 818 may correspond to a particular feature or capability of the programming device 702. For example, illustrative applications 818 may include one or more of a GUI application, data processing application, and/or stimulation parameter generation application.

It will be recognized that one or more processes and/or applications described herein may be implemented at least in part as computer-executable instructions, i.e., instructions executable by one or more computing devices, tangibly embodied in a computer-readable medium. In general, a processor (e.g., a microprocessor) receives instructions, e.g., from a memory, a computer-readable medium, etc., and executes those instructions, thereby performing one or more processes, including one or more of the processes described herein. Such instructions may be stored and transmitted using a variety of known computer-readable media.

A computer-readable medium (also referred to as a processor-readable medium) includes any medium that participates in providing data (e.g., instructions) that may be read by a computer (e.g., by a processor of a computer). Such a medium may take many forms, including, but not limited to, non-volatile media, volatile media, and transmission media. Non-volatile media may include, for example, optical or magnetic disks and other persistent memory. Volatile media may include, for example, DRAM, which typically constitutes a main memory. Transmission media may include, for example, coaxial cables, copper wire and fiber optics, including the wires that comprise a system bus coupled to a processor of a computer. Transmission media may include or convey acoustic waves, light waves, and electromagnetic emissions, such as those generated during RF and infrared IR data communications. Common forms of computer-readable media include, for example, a CD-ROM, a DVD, any other optical medium, a RAM, a PROM, an EPROM, a FLASH-EEPROM, any other memory chip or cartridge, or any other medium from which a computer can read.

As mentioned, the programming device 702 may be configured to adjust one or more gain parameters corresponding to one or more of the stimulation channels 218. Additionally or alternatively, the programming device 702 may be configured to direct the sound processor 106 to adjust one or more gain parameters corresponding to one or more of the stimulation channels 218.

Figure 9:
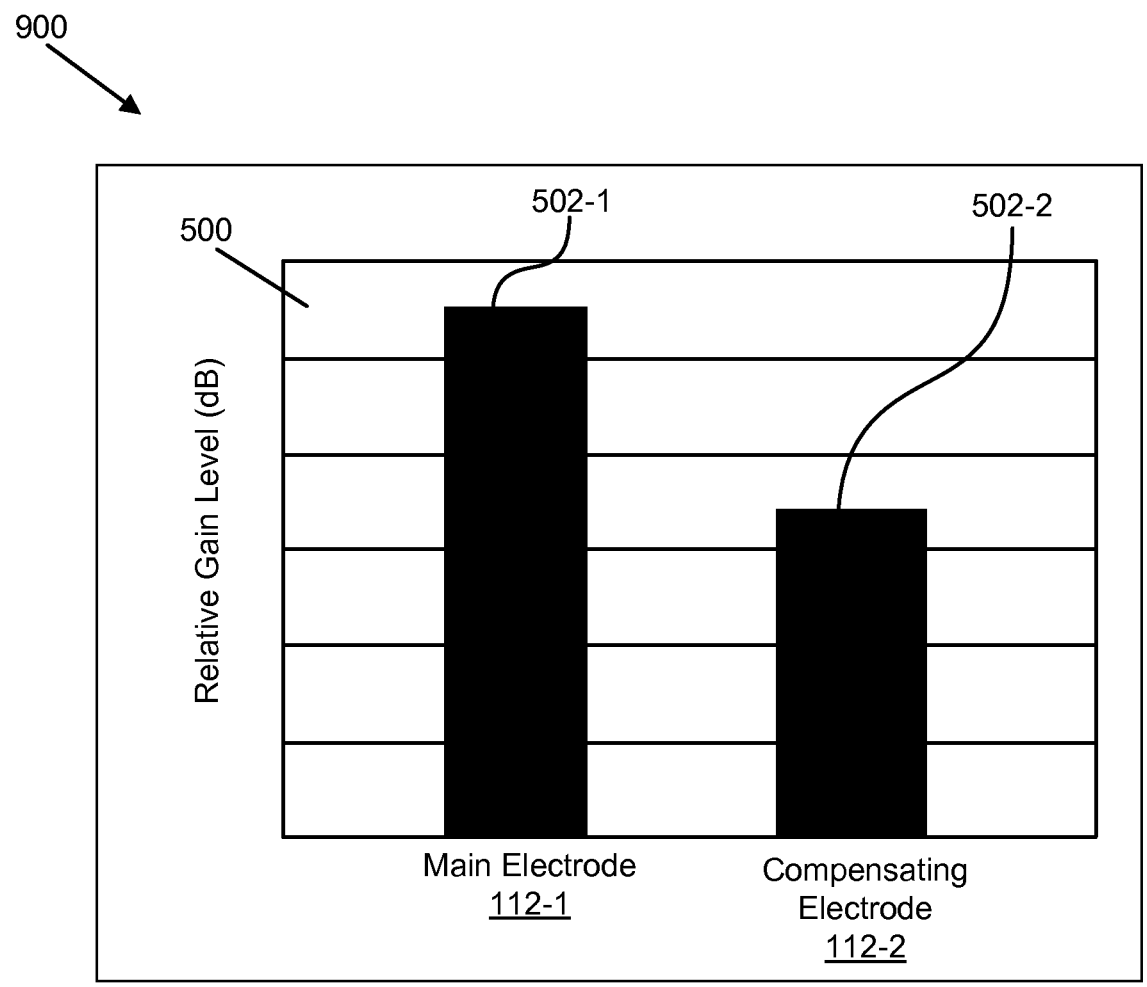
FIG. 9 shows a graphical user interface that may be displayed by a programming device and that is configured to facilitate adjustment of one or more gain parameters according to principles described herein.

In some examples, the programming device 702 may be configured to generate and display a GUI configured to facilitate adjustment of one or more stimulation parameters 702. For example, FIG. 9 shows an exemplary GUI 900 that may be displayed by programming device 702 and that is configured to facilitate adjustment of one or more stimulation parameters for a particular cochlear implant patient. As shown in FIG. 9, GUI 900 may include a depiction of graph 500 so that a clinician or other user thereof may visually see the relative gain levels of two or more electrodes 112 (e.g., electrodes 112-1 and 112-2).

A user may manually adjust one or more gain parameters 502 shown in GUI 900 in any suitable manner. For example, a clinician or other user may select a graphic representing a particular gain parameter 502 corresponding to a particular electrode, such as gain parameter 502-1. The user may then adjust the selected gain parameter 502-1 by adjusting a size of the selected graphic. In some examples, a user may use a mouse pointer or arrow key on a keyboard to drag or otherwise move the selected gain parameter 502-1 up or down, thereby increasing or decreasing the relative gain level of the selected gain parameter 502-1. Alternatively, a user may manually type in a desired relative gain level for the selected gain parameter 502-1.

In some embodiments, the user may select a ratio of the gain parameter 502-2 to the gain parameter 502-1 such that the user may adjust each of the gain parameters 502 in accordance with the selected ratio. Once the user has selected gain parameters 502 for a particular pitch, the sound processor 106 may automatically adjust the gain parameters 502 to obtain various other pitches in accordance with the above description.

Figure 10:
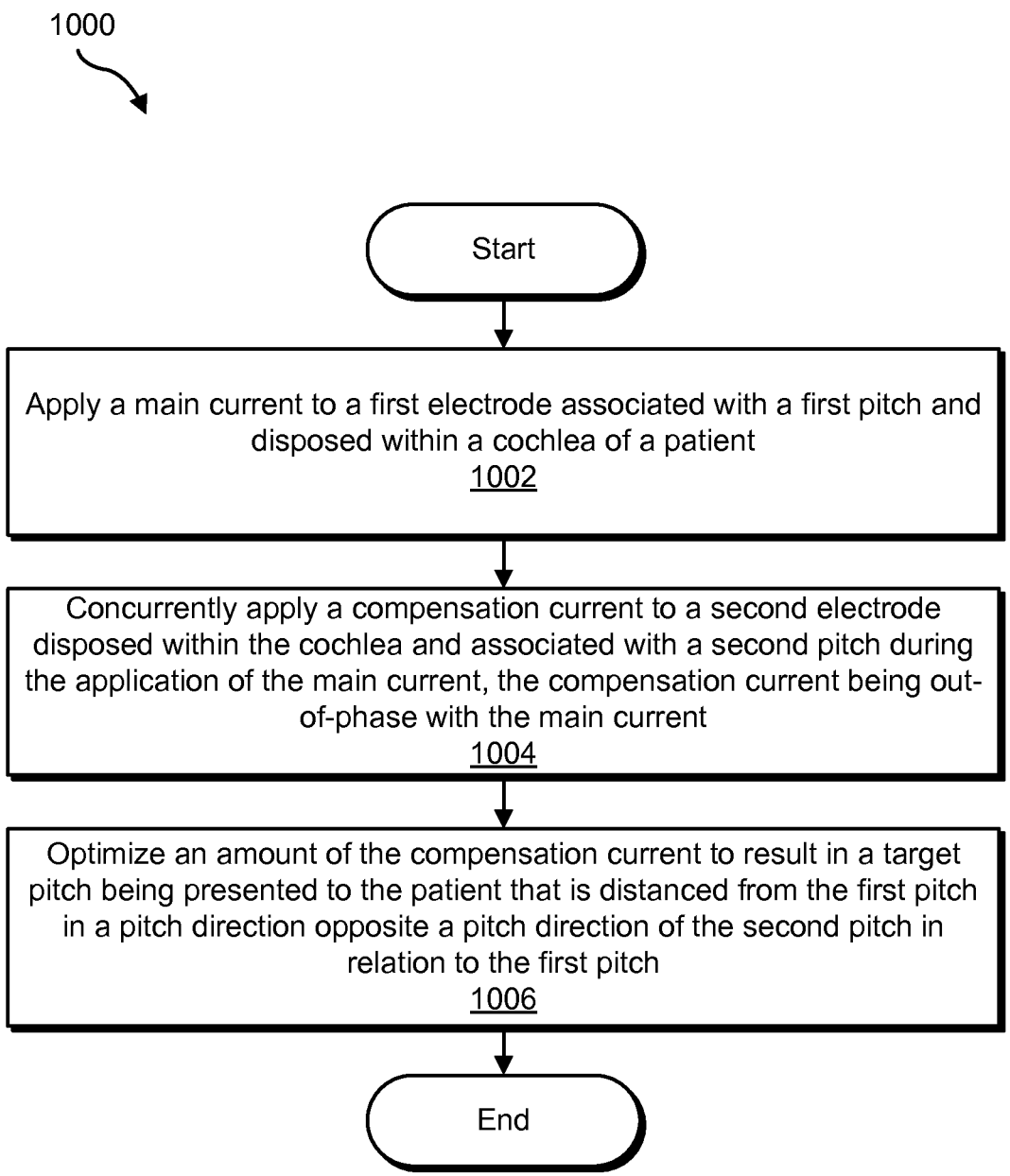
FIG. 10 illustrates an exemplary compensation current optimization method according to principles described herein.

FIG. 10 illustrates an exemplary compensation current optimization method 1000. Method 1000 may be alternatively referred to as a phantom electrode stimulation method. While FIG. 10 illustrates exemplary steps according to one embodiment, other embodiments may omit, add to, reorder, and/or modify any of the steps shown in FIG. 10. One or more of the steps shown in FIG. 10 may be performed by any of the systems, devices, and/or other components described herein. For example, one or more of the steps shown in FIG. 10 may be performed by cochlear implant system 100.

In step 1002, a main current is applied to a first electrode associated with a first pitch and disposed within a cochlea of a patient. The first electrode may include the most basal electrode, the most apical electrode, and/or any other electrode included within an array of electrodes disposed in the cochlea. The main current may be applied by implantable cochlear stimulator 110, for example, in any of the ways described herein.

In step 1004, a compensation current is concurrently applied to a second electrode disposed within the cochlea and associated with a second pitch during the application of the main current. The second electrode may be immediately adjacent to the first electrode and/or located at any other position in the electrode array as may serve a particular application. The compensation current may be out-of-phase with the main current, for example, and may be applied by implantable cochlear stimulator 110 in any of the ways described herein.

In step 1006, an amount of the compensation current is optimized to result in a target pitch being presented to the patient that is distanced from the first pitch in a pitch direction opposite a pitch direction of the second pitch in relation to the first pitch. The compensation current may be optimized in any of the ways described herein. For example, the compensation current may be optimized to result in a target pitch that is higher than the first electrode. Alternatively, the compensation current may be optimized to result in a target pitch that is lower than the first electrode.

Figure 11:
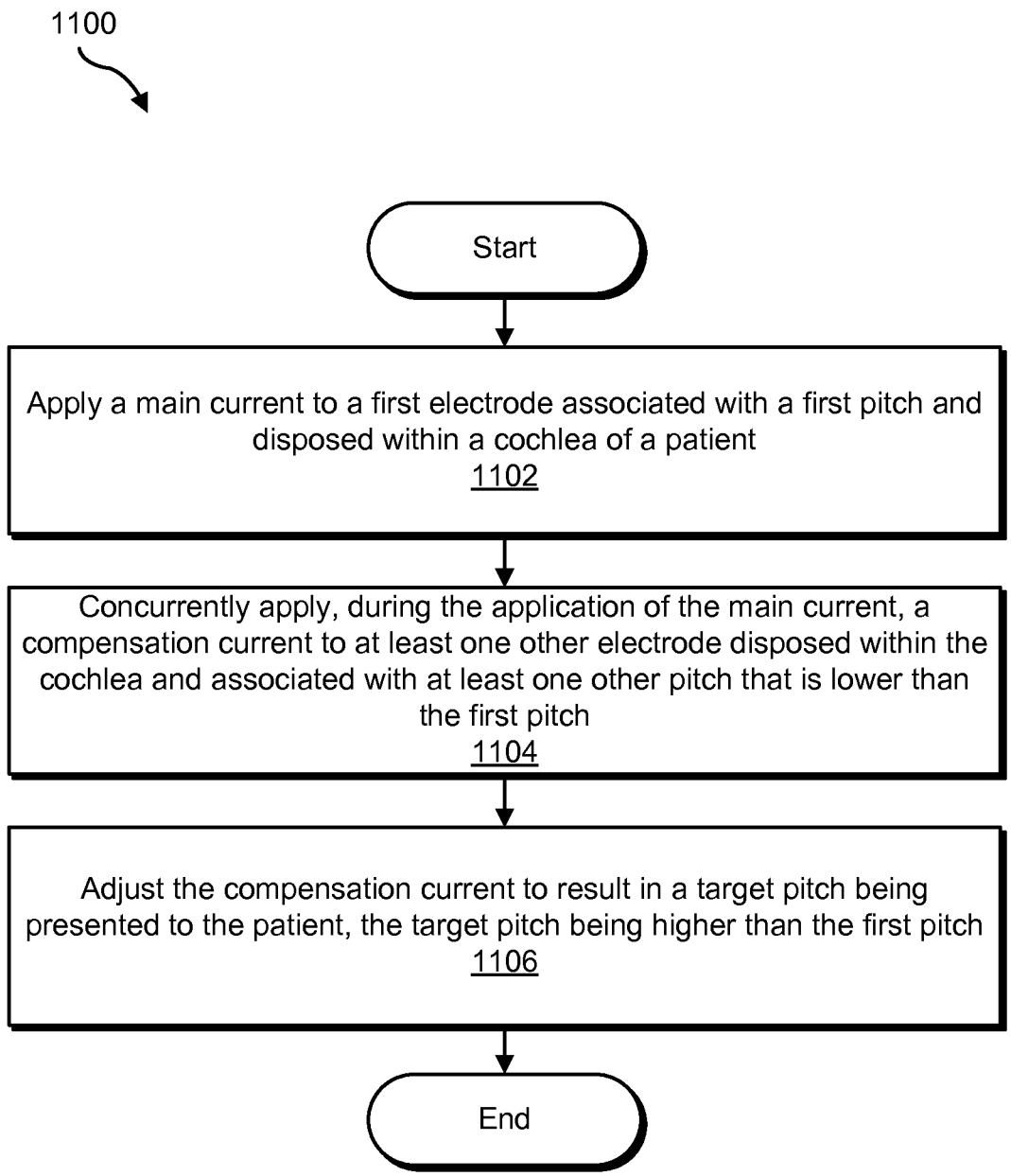
FIG. 11 illustrates an exemplary phantom electrode stimulation method according to principles described herein.

FIG. 11 illustrates an exemplary phantom electrode stimulation method 1100. While FIG. 11 illustrates exemplary steps according to one embodiment, other embodiments may omit, add to, reorder, and/or modify any of the steps shown in FIG. 11. One or more of the steps shown in FIG. 11 may be performed by any of the systems, devices, and/or other components described herein. For example, one or more of the steps shown in FIG. 11 may be performed by cochlear implant system 100.

In step 1102, a main current is applied to a first electrode associated with a first pitch and disposed within a cochlea of a patient. The first electrode may include a most basal electrode included in an array of electrodes disposed in the cochlea or any other electrode included in the electrode array.

In step 1104, a compensation current is concurrently applied during the application of the main current to at least one other electrode disposed within the cochlea and associated with at least one other pitch that is lower than the first pitch. The at least one other electrode may include any number of electrodes in the array of electrodes as may serve a particular implementation. The compensation current may be concurrently applied in any of the ways described herein.

In step 1106, the compensation current is adjusted to result in a target pitch being presented to the patient, the target pitch being higher than the first pitch. The compensation current may be adjusted in any of the ways described herein.

Figure 12:
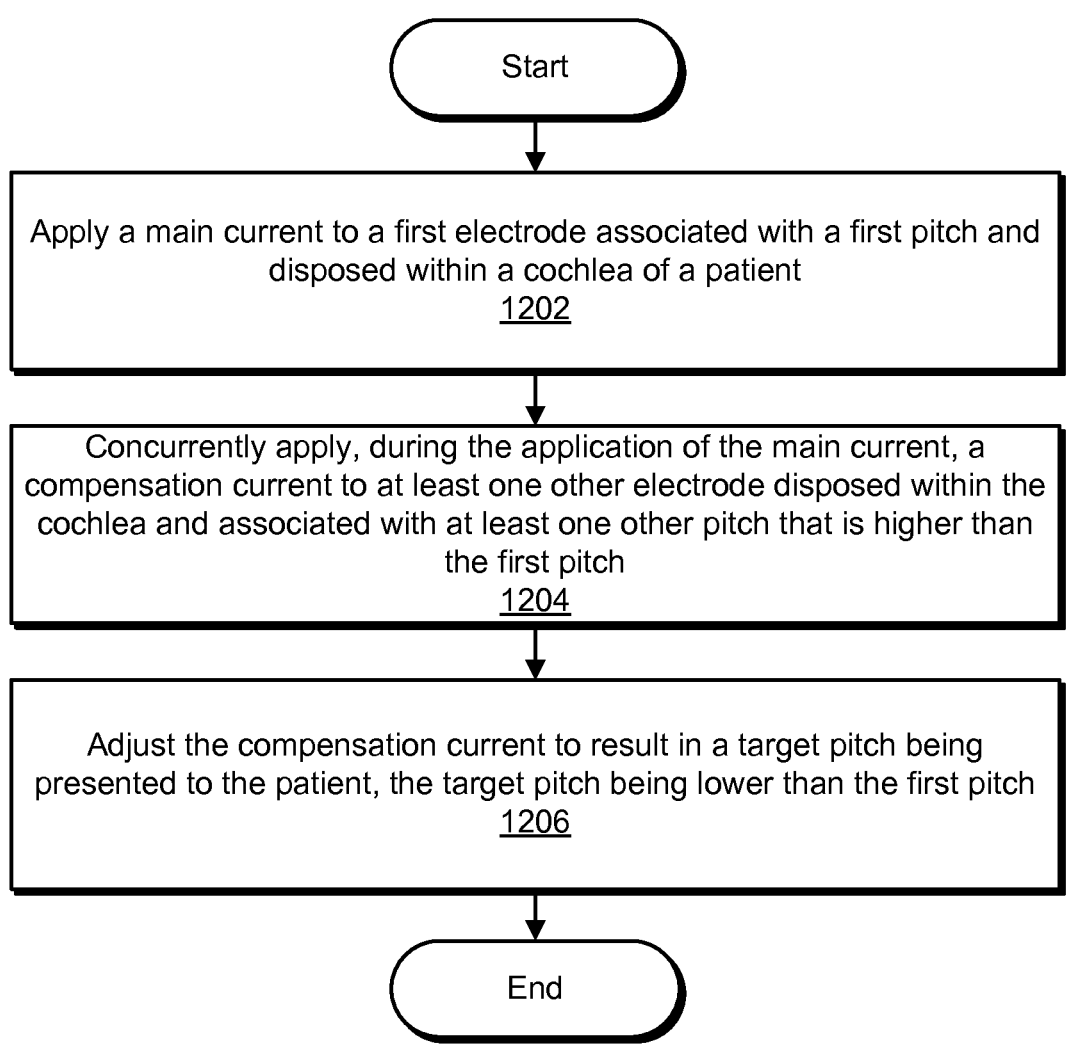
FIG. 12 illustrates another exemplary phantom electrode stimulation method according to principles described herein.

FIG. 12 illustrates another phantom electrode stimulation method 1200. While FIG. 12 illustrates exemplary steps according to one embodiment, other embodiments may omit, add to, reorder, and/or modify any of the steps shown in FIG. 12. One or more of the steps shown in FIG. 12 may be performed by any of the systems, devices, and/or other components described herein. For example, one or more of the steps shown in FIG. 12 may be performed by cochlear implant system 100.

In step 1202, a main current is applied to a first electrode associated with a first pitch and disposed within a cochlea of a patient. The first electrode may include a most apical electrode included in an array of electrodes disposed in the cochlea or any other electrode included in the electrode array.

In step 1204, a compensation current is concurrently applied during the application of the main current to at least one other electrode disposed within the cochlea and associated with at least one other pitch that is higher than the first pitch. The at least one other electrode may include any number of electrodes in the array of electrodes as may serve a particular implementation. The compensation current may be concurrently applied in any of the ways described herein.

In step 1206, the compensation current is adjusted to result in a target pitch being presented to the patient, the target pitch being lower than the first pitch. The compensation current may be adjusted in any of the ways described herein.

In some examples, the degree or amount of compensation current applied to a compensating electrode (e.g., electrode 112-2) may be varied to vary the amount of pitch shift produced by the phantom electrode stimulation. In this manner, real time changes in the low or high frequency information of an acoustic spectrum of an audio signal (e.g., time to time variation in fundamental frequency of the acoustic spectrum) outside the range of frequencies associated with the electrodes 112 may be mimicked.

Phantom electrode stimulation may be beneficial in some listening conditions (also referred to as "auditory scenes"), but detrimental in other listening conditions. As used herein, a "listening condition" or "auditory scene" refers to a particular auditory or listening environment of a cochlear implant patient. For example, an auditory scene may be representative of a crowded restaurant, wind, noise from an airplane or automobile, music, speech, a quiet bedroom, and/or any other auditory environment that a cochlear implant patient may experience.

Hence, in some examples, one or more components described herein (e.g., sound processor 106 and/or programming device 702) may be configured to detect or recognize an auditory scene and adjust, enable, or disable phantom electrode stimulation accordingly. For example, sound processor 106 may adjust an amount of compensation current applied via one or more compensating electrodes in response to a detected auditory scene.

Sound processor 106 and/or programming device 702 may detect an auditory scene in accordance with a predefined detection heuristic. An example of such a heuristic is a heuristic based on a band-by-band spectral power time variance of the power spectrum. Additionally or alternatively, the auditory scene may be detected by sound processor 106 and/or programming device 702 in response to patient input. For example, a patient may recognize a particular auditory scene and input a description of the auditory scene into a graphical user interface provided by programming device 702.

Once an auditory scene is detected, sound processor 106 and/or programming device 702 may adjust, enable, or disable phantom electrode stimulation based on the detected auditory scene. For example, it may be desirable to enable phantom electrode stimulation (i.e., apply compensation current to one or more compensating electrodes) when a patient is listening to music and disable phantom electrode stimulation (i.e., cease applying compensation current to one or more compensating electrodes) when the patient is listening to speech.

The preceding description has been presented only to illustrate and describe embodiments of the invention. It is not intended to be exhaustive or to limit the invention to any precise form disclosed. Many modifications and variations are possible in light of the above teaching.

What is claimed is:

1. A system comprising:
    a sound processor configured to process one or more audio signals; and
    an implantable cochlear stimulator communicatively coupled to the sound processor and configured to apply stimulation representative of the one or more audio signals to a patient via a plurality of electrodes;
    wherein the sound processor directs the implantable cochlear stimulator to
    apply a main current to a first electrode included in the plurality of electrodes and associated with a first pitch,
    concurrently apply, during the application of the main current, a compensation current to a second electrode included in the plurality of electrodes and associated with a second pitch that is lower than the first pitch; and
    adjust the compensation current to result in a target pitch being presented to the patient, the target pitch being higher than the first pitch.

2. The system of claim 1, wherein the sound processor directs the implantable cochlear stimulator to concurrently apply, during the application of the main current, the compensation current to a third electrode included in the plurality of electrodes and associated with a third pitch that is lower than the first pitch.

3. The system of claim 2, wherein the implantable cochlear stimulator concurrently applies the compensation current to the second electrode and to the third electrode by:
    applying a primary compensation current to the second electrode; and
    applying a secondary compensation current to the third electrode;
    wherein the primary compensation current is out-of-phase with the main current and wherein the secondary compensation current is out-of-phase with the primary compensation current.

4. The system of claim 1, wherein the first and second electrodes are disposed within a cochlea of the patient.

5. The system of claim 4, wherein the first electrode comprises a most basal electrode included in the plurality of electrodes.

6. The system of claim 1, wherein the sound processor directs the implantable cochlear stimulator to adjust the compensation current by identifying an amount of the main current when the main current is at a most comfortable current level and an amount of the compensation current is substantially equal to zero.

7. The system of claim 6, wherein the sound processor directs the implantable cochlear stimulator to adjust the compensation current by further selecting a ratio of the compensation current to the main current that results in another most comfortable current level.

8. The system of claim 7, wherein the sound processor directs the implantable cochlear stimulator to adjust the compensation current by further:
identifying a coefficient k by using an equation represented by $I(\sigma)=I(0)/(1-(k*\sigma))$; and
using the equation to adjust the main current and the compensation current to obtain the target pitch while maintaining the another most comfortable current level;
wherein
I(0) represents the amount of the main current when the main current is at the most comfortable current level and the amount of the compensation current is substantially equal to zero,
$\sigma$ represents the ratio of the compensation current to the main current, and
$I(\sigma)$ represents the amount of the main current as a function of $\sigma$.

9. The system of claim 1, wherein the sound processor is external to the patient.

10. The system of claim 1, wherein one or more portions of the sound processor are implanted within the patient.

11. A system comprising:
a sound processor configured to process one or more audio signals; and
an implantable cochlear stimulator communicatively coupled to the sound processor and configured to apply stimulation representative of the one or more audio signals to a patient via a plurality of electrodes;
wherein the sound processor directs the implantable cochlear stimulator to
apply a main current to a first electrode included in the plurality of electrodes and associated with a first pitch,
concurrently apply, during the application of the main current, a compensation current to a second electrode included in the plurality of electrodes and associated with a second pitch that is higher than the first pitch; and
adjust the compensation current to result in a target pitch being presented to the patient, the target pitch being lower than the first pitch.

12. The system of claim 11, wherein the sound processor directs the implantable cochlear stimulator to concurrently apply, during the application of the main current, the compensation current to a third electrode disposed within the patient and associated with a third pitch that is higher than the first pitch.

13. The system of claim 12, wherein the implantable cochlear stimulator concurrently applies the compensation current to the second electrode and to the third electrode by:
applying a primary compensation current to the second electrode; and
applying a secondary compensation current to the third electrode;
wherein the primary compensation current is out-of-phase with the main current and wherein the secondary compensation current is out-of-phase with the primary compensation current.

14. The system of claim 11, wherein the first and second electrodes are disposed within a cochlea of the patient.

15. The system of claim 14, wherein the first electrode comprises a most apical electrode included in the plurality of electrodes.

16. The system of claim 11, wherein the sound processor directs the implantable cochlear stimulator to adjust the compensation current by identifying an amount of the main current when the main current is at a most comfortable current level and an amount of the compensation current is substantially equal to zero.

17. The system of claim 16, wherein the sound processor directs the implantable cochlear stimulator to adjust the compensation current by further selecting a ratio of the compensation current to the main current that results in another most comfortable current level.

18. The system of claim 17, wherein the sound processor directs the implantable cochlear stimulator to adjust the compensation current by further:
identifying a coefficient k by using an equation represented by $I(\sigma)=I(0)/(1-(k*\sigma))$; and
using the equation to adjust the main current and the compensation current to obtain the target pitch while maintaining the another most comfortable current level;
wherein
I(0) represents the amount of the main current when the main current is at the most comfortable current level and the amount of the compensation current is substantially equal to zero,
$\sigma$ represents the ratio of the compensation current to the main current, and
$I(\sigma)$ represents the amount of the main current as a function of $\sigma$.

19. The system of claim 11 wherein the sound processor is external to the patient.

20. The system of claim 11, wherein one or more portions of the sound processor are implanted within the patient.

* * * * *